United States Patent
Jacobs

(10) Patent No.: US 9,126,061 B2
(45) Date of Patent: Sep. 8, 2015

(54) ANTIOXIDANT COMPOSITIONS FOR THE CLEANSING AND CONDITIONING OF SKIN

(75) Inventor: June Jacobs, New York, NY (US)

(73) Assignee: June Jacobs Laboratories, LLC

( * ) Notice: Subject to any disclaimer, the term of this patent is extended or adjusted under 35 U.S.C. 154(b) by 412 days.

(21) Appl. No.: 12/615,842

(22) Filed: Nov. 10, 2009

(65) Prior Publication Data

US 2010/0119463 A1    May 13, 2010

Related U.S. Application Data

(60) Provisional application No. 61/114,019, filed on Nov. 12, 2008.

(51) Int. Cl.
| | | |
|---|---|---|
| *A61K 36/00* | (2006.01) | |
| *A61K 36/815* | (2006.01) | |
| *A61K 36/87* | (2006.01) | |
| *A61K 36/82* | (2006.01) | |
| *A61K 36/73* | (2006.01) | |
| *A61Q 19/08* | (2006.01) | |
| *A61K 8/04* | (2006.01) | |
| *A61K 8/06* | (2006.01) | |
| *A61K 8/97* | (2006.01) | |
| *A61Q 19/10* | (2006.01) | |

(52) U.S. Cl.
CPC ............... *A61Q 19/08* (2013.01); *A61K 8/042* (2013.01); *A61K 8/062* (2013.01); *A61K 8/064* (2013.01); *A61K 8/97* (2013.01); *A61Q 19/10* (2013.01); *A61K 2800/522* (2013.01)

(58) Field of Classification Search
CPC ..... A61K 36/00; A61K 36/815; A61K 36/81; A61K 36/87; A61K 36/82; A61K 36/73
USPC .......................... 434/729, 766, 777, 757, 765
See application file for complete search history.

(56) References Cited

U.S. PATENT DOCUMENTS 5,916,573 A * 6/1999 Spiers et al. .................. 424/401
2005/0287278 A1 12/2005 Quan et al.

2007/0166267 A1 7/2007 Majewski et al.
2008/0171031 A1 7/2008 Jochim et al.
2008/0175931 A1 7/2008 Schlemer et al.

FOREIGN PATENT DOCUMENTS

| DE | 10013167 A1 | | 9/2001 | |
|---|---|---|---|---|
| EP | 0659402 A2 | | 6/1995 | |
| KR | 20020070201 | * | 3/2009 | ............... A61K 7/48 |
| WO | WO 99/33439 | * | 7/1999 | ............... A61K 7/42 |

OTHER PUBLICATIONS

Copeland et al. Change your Looks, Change Your Life: Quick Fixes and Cosmetic Surgery Solutions for Looking Younger, Feeling Healthier, and Living Better. HarperCollins. 2004. p. 69.*
The Herbal Encyclopedia. Retrieved from the internet. <http://web.archive.org/web/20030210135948/http://www.naturalark.com/herbcomb.html>. Web archive date Feb. 10, 2003. Retrieved on Jun. 1, 2011. 7 Pages.*
Zhao et al. Photoprotective Effect of Black Tea Extracts Against UVB-Induced Phototoxicity in Skin. Photochemistry and Photobiology. Oct. 1999; 70, 4. pp. 637-644.*
Askedweb.com. Retrieved from the internet. <http://askedweb.com/Julie/posts/1469-Get-Rid-Of-Cellulite>. Apr. 9, 2007. Retrieved on Jun. 1, 2011. 10 Pages.*
Instablogs. Goji Berries, Most Powerful Antioxidant for Topical Creams. Sep. 29, 2006. Retrieved from the internet. <http://esther.instablogs.com/entry/goji-berries-most-powerful-antioxidant-for-topical-creams/>. Retrieved on Jun. 1, 2011. 2 Pages.*
Zhao et al., "Lycium barbarum glycoconjugates: effect on human skin and cultured dermal fibroblasts", J. Phytomedcine, vol. 12, No. 1-2, Jan. 10, 2005, pp. 131-137.
Database WPI Week 200369 Thomas Scientific, London, GB; AN 2003-728134 & KR 2003 0025868 A (Hanacos Co Ltd), Mar. 29, 2003, 1 page.

* cited by examiner

*Primary Examiner* — Chris R Tate
*Assistant Examiner* — Deborah Davis
(74) *Attorney, Agent, or Firm* — Mintz Levin Cohn Ferris Glovsky and Popeo, P.C.; Muriel Liberto, Esq.

(57) ABSTRACT

Antioxidant cosmetic skin care compositions formulated to combat conditions associated with free radical damage and oxidative stress are provided. The compositions contain effective amounts of one of several active agents, including an agent derived from one or more of the plant species: *Lycium barbarum, Punica granatum, Vitis vinifera, Aspalathus linearis,* and *Camellia Sinensis* as well as cosmetically acceptable carriers. These cosmetic compositions find use in improving the appearance of aged or damaged skin.

11 Claims, No Drawings

ANTIOXIDANT COMPOSITIONS FOR THE CLEANSING AND CONDITIONING OF SKIN

CROSS REFERENCE TO RELATED APPLICATIONS

This application claims the benefit of priority under 35 U.S.C. §119 to U.S. Provisional Patent Application Ser. No. 61/114,019, filed on Nov. 12, 2008, entitled, "ANTIOXIDANT COMPOSITIONS FOR THE CLEANSING AND CONDITIONING OF SKIN", the entire disclosures of which is incorporated by reference herein.

BACKGROUND

Free radicals are reactive ion species that include unpaired electrons. These unpaired electrons are very unstable and may react rapidly with other surrounding molecules so as to achieve their own stabilization. Oxygen, for instance, often forms a reactive oxygen ionic species (ROS). ROS are free radicals that react with surrounding molecules, for instance, within tissues of a body, and transform the cell structures of which they are a part. As the function and shape of the transformed tissues are altered, the molecules that make up the affected tissue may in turn be transformed and turned into free radicals. In this manner, a destructive chain reaction is initiated, which chain reaction can be very damaging to the skin.

More specifically, free radicals work quickly to trigger chain reactions that may produce thousands of additional free radicals. The damage caused can range from cell damage to ultimate cell death. With respect to the surface of the skin, free radical damage may result in cellular breakdown that manifests itself superficially in lines, wrinkles, dry skin, loss of elasticity, and skin discoloration. With respect to the deeper levels of the skin tissue, free radical propagation may substantially destroy the collagen and elastin support system, damage vital cellular proteins and enzymes, degrade DNA, impair critical immune functions, and cause general tissue deterioration. The reactivity of various free radicals and the burden they place on the body in defending against the evolution of pathological conditions is known as oxidative stress. Oxidative stress and the likelihood of damage caused by reactive oxygen species (ROS) increases with age.

Free radical scavengers or antioxidants are known to help reverse and prevent free radical damage. Antioxidants are chemical species that prevent oxidation caused by free radicals. Specifically, anti-oxidants have the ability to donate electrons to a free radical without themselves forming a free-radical, thus, breaking the damaging chain reaction indicative of unfettered free radical propagation. When applied topically to the skin, antioxidants interact with free radicals in the tissues in such a way as to render them harmless before they can react and cause damage to other molecules and tissues, thus preventing destructive chain reactions from forming. Accordingly, topical compositions containing antioxidants have the capability of interrupting or even preventing the cellular onslaught caused by reactive oxygen species and other free radicals.

Accordingly, there is a continued need to develop new skin care products containing antioxidants that can be more effectively delivered so as to increase the aesthetic and protective benefits offered by this class of compounds. Therefore, herein is presented a novel antioxidant skin care composition that is designed to reverse and/or prevent the damaging effects of free radicals, cleanse and rejuvenate the skin, as well as promote and prolong a more healthy, youthful appearance.

SUMMARY OF THE DISCLOSURE

The present invention features a novel cosmetic composition for protecting the skin from environmental factors leading to cellular breakdown and oxidative stress as well as enhancing the appearance, condition, and elasticity of the skin. The topical skin care compositions of the disclosure not only promote the free radical scavenging potential of the skin, they also cleanse and condition the skin as well as increase its natural luster and smoothness. The topical compositions include synergistic combinations of antioxidant and natural emollient ingredients that are specially formulated to combat and reduce oxidative stress caused by free radical damage as well as to cleanse and recondition the skin.

Accordingly, the present disclosure features antioxidant cosmetic skin care compositions that include a combination of natural ingredients which function in a synergistic manner to combat oxidative stress and to rejuvenate the skin. In certain variations, the compositions include cosmetically effective amounts of one or a combination of several active agents derived from *Lycium barbarum*, *Punica granatum*, *Vitis vinifera*, *Aspalathus linearis*, and *Camellia Sinensis*. The antioxidant skin care constituents of the present disclosure may be combined with one or more cosmetically acceptable vehicle(s) so as to produce formulations that may be applied topically to the skin in such a manner as to decrease oxidative stress, reduce skin irritation and inflammation, as well as to promote a more vitalized, healthy, and youthful appearance. The cosmetic formulations of the disclosure may further be combined with one or more vasodilators, anti-inflammatories, or analgesics and/or may additionally include skin soothing and moisturizing agents.

DETAILED DESCRIPTION OF THE EMBODIMENTS

Topical skin care compositions are herein provided for the cleansing and conditioning of the skin as well as for the repairing and/or preventing of damage associated with disruptions caused by harmful exposure to environmental factors and other inflammatory aggravators that may lead to oxidative stress within the skin. The skin care compositions of the invention include synergistic combinations of cosmetically effective amounts of various antioxidant and/or emollient ingredients that are formulated to prevent or reverse a variety of aging-related conditions of the skin that may have reactive oxygen species (ROS) and other free radical reactions as an underlying cause of the condition. Accordingly, an effective amount of a topical composition of the disclosure may be used to cleanse and condition the skin as well as to repair and/or protect the skin from various conditions, such as e.g., the appearance of aging, dry skin, dermatitis, eczema, sunburn, inflammation, pruritic lesions, and other inflammatory and non-inflammatory lesions of the skin of a subject.

By a "cosmetically effective amount" (e.g., of an antioxidant skin care composition of the disclosure) is meant a quantity of the composition provided for topical administration and at a particular dosing regimen which is sufficient to achieve a desired appearance, feel, and/or protective effect. For example, an amount that results in the prevention of or a decrease in the symptoms associated with an undesired condition. The amount of the antioxidant composition to be administered to the subject will depend on the type and severity of the condition, the amenability of the condition to respond to the formulated antioxidants, and on the characteristics of the subject and the subject's metabolic ability to respond to the synergistic antioxidant compositions of the disclosure; such characteristics include general health, age, sex, body weight, skin condition, and tolerance to the active agents in the compositions. The skilled practitioner will be able to determine appropriate dosages depending on these and other factors.

The term "subject," as used herein, may be a mammal, such as a human, but may also be an animal, e.g., domestic animals (e.g., dogs, cats and the like), farm animals (e.g., cows, sheep, pigs, horses and the like) and laboratory animals (e.g., rats, mice, guinea pigs and the like).

Without being held to theory, the present cosmetic compositions are based on the discovery by the inventors that the combination of the various anti-oxidant and/or emollient agents herein detailed can be formulated into cosmetic topical compositions that are effective in reducing the amount of damage caused by free radicals and oxidative stress, while at the same time being both less prone to problematic side-effects as compared other such compositions and more rejuvenating for the skin.

To protect against such environmental factors as over exposure to the sun, pollution, bacterial and viral infection, the body, and in particular the skin, has developed a natural cellular defense system that includes the production of free radical scavengers, such as antioxidants. By producing antioxidants that are capable of reacting with and enzymatically converting free radicals to less or non-reactive chemical species, the body can decrease the damage caused by oxidative stress. Accordingly, part of the body's natural defense system is the production of a group of enzymes that act as anti-oxidants.

Three enzymes that act as free radical scavengers that the body naturally produces include: superoxide dismutase (SOD), catalase (CAT), and glutathione peroxidase (GPX). These enzymes are capable of reacting with free radicals, such as reactive oxygen species (ROS), in such a way that the free radical species is reduced, while at the same time the free radical scavenging enzyme is not itself oxidized. Hence, these enzymes are not consumed in their interaction with free radicals.

It has been found that the active agents of the disclosure contain natural ingredients that are able to interact with the cells of the body in such a way as to increase the body's natural antioxidant self-defense mechanisms. Specifically, without being held to theory, it is believed that the compositions of the invention not only act as free radical scavengers in and of themselves, but also increase the potential of the skin to produce endogenous free radical scavengers such as SOD, CAT, and GPX. An increase in free radical scavengers leads to a decrease in free radical activity, which results in a decrease in the level of harmful oxidants in the skin. The end result is that a subject's skin that is treated with the compositions of the invention appears to be healthier, more vibrant looking, and more resilient when faced with harmful environmental aggravators than skin that is not treated. Accordingly, the compositions of the invention create an overall decrease in the oxidative stress and inflammation experienced by the skin and result in a more youthful appearance when applied topically.

Accordingly, one aspect of the present invention is to provide rejuvenating cosmetic compositions that include natural antioxidants and emollients. The antioxidant compositions of the invention are to be topically applied to the skin. Suitable compositions of the invention are derived from natural sources that individually have been found to increase the body's potential to relieve oxidative stress and reduce inflammation when taken orally. Specifically, the individual ingredients herein provided have been found to be useful in a combination formulation that when applied topically to the body protect the skin from oxidative stress while also increasing the skin's natural protections against free radical damage without the untoward side effects that may be experienced by oral administration.

Therefore, another aspect of the present disclosure is to provide cosmetic compositions that may be formulated for topical administration and applied to the skin so as to both reduce oxidative stress and rejuvenate the skin. In another embodiment, the topical formulations may be applied to the skin so as to increase the skin cells natural production of beneficial antioxidants, such as SOD, CAT, and GPX. In a further embodiment, the topical compositions may be applied to the skin so as to clean the skin and give it a more vibrant, youthful appearance and to decrease the indicia of aging, e.g., the appearance of wrinkles, inflammation, abrasions, and lesions.

These and other aspects of the present disclosure will be more readily apparent and understood by considering the following description.

Components of the Cosmetic Compositions

The compositions contemplated for use in the present compositions include a mixture of various plant derived ingredients and/or active agents that have been formulated in conjunction with a cosmetically acceptable vehicle so as to be applied topically to the skin to clean, rejuvenate, reduce oxidative stress, and/or generally improve the appearance of the skin. The plant varieties found to be useful in accordance with the invention are set forth and described herein below.

*Lycium barbarum*, also known as wolfberry or goji berry, is part of the Solanacea family. Like other members of the *Lycium* genus, goji berry is a deciduous woody perennial plant. These species produce a bright orange-red ellipsoid berry containing a number of seeds. The fruit of goji berry plants have typically been eaten raw or have been processed into juices, wines, or brewed into herbal teas. The seeds, leaves, and root bark of the goji berry have also been used to make teas. Extracts from the fruit, leaves, seeds, and roots have been orally administered in various ministrations so as to enhance the immune system, improve liver function, reduce inflammation, as an anti-bacterial and anti-fungal medicine, as well as to promote general health. Additionally, polysaccharides and zeaxanthin derived from goji berry have been shown to act as an antioxidants both in vitro and in vivo when administered orally. See, for instance, Li, X M et al., J. Ethnopharmacol. 2007; 111(3):504-11. Accordingly, one or more of the fruit, leaves, seeds, and roots of the goji berry may be processed into active agents or an extract thereof may be processed, by means well known in the art, and used by itself or in conjunction with the other ingredients disclosed herein to from a topical composition of the disclosure. For instance, in various exemplary embodiments, one or more of ascorbic acid, beta-carotene, riboflavin, and/or minerals (such as Ca, Cu, Fe, Mg, Mn, K, Na) derived from extracts of the goji berry may be included in a composition of the disclosure. Additionally, whole fruit extracts derived from the goji berry may be included as a component of a composition of the disclosure. Such compositions evidence enhanced antioxidant benefits. Other Solanacea family members that may be processed to produce active agents that may be used in the composition of the disclosure include: *Lycium chinense, Lycium halimifolium, Lycium ovatum, Lycium turbinatum*, and also *Lycium vulgare*.

*Punica granatum*, also known as a pomegranate, is part of the Lythraceae family. Like other members of the *Punica* genus, the pomegranate plant is a deciduous shrub or small tree. These species produce a bright red flower and fruits containing a number of aril seeds. The fruit of pomegranate plants have typically been eaten raw or have been processed into juices, wines, or made into syrups. The juice of the aril seeds of the pomegranate have been orally administered in various ministrations so as to reduce the risk of heart disease and atherosclerosis as well as to reduce oxidative stress. Additionally, polyphenols and tannins (e.g., punicalagins) extracted or otherwise derived from the pomegranate have been known to act as antioxidants when administered orally, to treat cancer, cardiovascular disease, diabetes, infection, and the like. See, for instance, Jurenka, J. S., Altern. Med. Rev. 2008; 13(2):128-44. Accordingly, one or more of the fruit or an extract derived from the pomegranate may be processed in to active agents, by means well known in the art, that may be used by themselves or in conjunction with the other ingredients disclosed herein to from a topical composition of the disclosure. For instance, in various exemplary embodiments, one or more of ellagitannin, polyphenol, riboflavin, and/or tannin extracts derived from the pomegranate may be included in a composition of the disclosure. Additionally, whole fruit extracts derived from the pomegranate may be included as a component of a composition of the disclosure. Such compositions evidence enhanced antioxidant benefits. Other *Punicia* members that may be processed to produce active agents that may be used in the composition of the disclosure include: *Punica garantum nana* and *Punica protopunica*.

*Vitis vinifera*, also known as the grape vine, is part of the Vitaceae family. Like other members of the *Vitis* genus, the grape vine is a liana with flaky bark that may grow up to about 35 m tall. These species produce big, broad leaves and a fruit, called the grape, which may or may not have seeds. The grapes may be green, red, or purple. The fruit of the grape vine have typically been eaten raw or have been processed into juices, wines, and fruit spreads. The seeds, leaves, and grapes of the grape vine have been processed and orally administered in various ministrations so as to prevent inflammation; reduce the risk of cancer, kidney, and liver disease; as well as to provide the body with antioxidants. For instance, flavonoids derived from the fruit of the grape vine have been shown to act as an antioxidant. See, for instance, Sudheesh, S. et al. Fitoterapia, 2005; 76(2):181-186. Accordingly, one or more of the fruit, leaves, and seeds of the grape vine may be processed themselves into active agents or an extract thereof may be processed, by means well known in the art, and used by itself or in conjunction with the other ingredients disclosed herein to from a topical composition of the disclosure. For instance, in various exemplary embodiments, a polyphenol extract derived from the grape seed may be included within a composition of the disclosure. Such compositions evidence enhanced antioxidant benefits. Other members of the *Vitis* genus may be processed to produce active agents that may be used in the composition of the disclosure.

*Aspalathus linearis*, also known as rooibos, is part of the Fabaceae family. Like other members of the *Aspalathus* genus, rooibos is a member of the legume family of plants with bushy leaves and yellow flowers. The leaves and/or stems of the rooibos are typically oxidized and processed to produce a tea called "Red Tea" or "African Red Tea." The non-oxidized leaves may be processed to make a green tea. Rooibos teas and extracts have been orally administered in various ministrations to act as an antioxidant. For instance, polyphenols and flavonoids of rooibos contain aspalathin and nothofagin that are known to act as antioxidants when administered orally. See, for instance, Mackay, D L., et al. Phytother Res. 2007; 21(1):1-6. Accordingly, one or more of the flowers, leaves, and roots of the rooibos plant may be processed themselves into active agents or an extract thereof may be processed, by means well known in the art, and used by itself or in conjunction with the other ingredients disclosed herein to from a topical composition of the disclosure. For instance, in various exemplary embodiments, a polyphenol and/or other phytochemical extract derived from the African Red. Tea leaf may be included within a composition of the disclosure. Such compositions evidence enhanced antioxidant benefits. Other members of the *Aspalathus* genus and/or *Cyclopia intermedia* species may be processed to produce active agents that may be used in the composition of the disclosure.

*Camellia Sinensis*, also known as the tea plant, is part of the Theaceae family. Like other members of the *Camellia* genus, the tea plant is an evergreen, leafy small tree with yellow-white flowers. The leaves and/or stems of the tea plant are typically processed to produce tea. Dependent on the processing, the time and level of oxidation, white tea, green tea, oolong, black tea as well as yellow tea may be produced. The tea leaves used to produce black tea are oxidized for a long period of time, where as the young, minimally oxidized tea leaves are used to produce white tea. Tea plant teas and extracts have been orally administered in various ministrations to treat asthma, peripheral vascular disease, and coronary artery disease as well as other conditions. Green and black teas have also been found to be rich in antioxidants. See, for instance, Antonello, M. Am. J. Hypertens. 2007; 20(12): 1321-8 and Bhattacharyya, A. J. Environ. Pathol. Toxicol. Oncol. 2007; 26(4):245-54. Accordingly, one or more of the flower, leaves, stems, and roots of the tea plant may be processed into active agents or an extract thereof may be processed, by means well known in the art, and used by itself (e.g., as white, green, black, and/or yellow tea) or in conjunction with the other ingredients disclosed herein to from a topical composition of the disclosure. For instance, in various exemplary embodiments, a polyphenol extract of one or more of the tea plants disclosed herein (e.g., a white, green, black, and/or yellow tea polyphenol tea extract) may be included within a composition of the disclosure. Additionally, extracts derived from the leafs of one or more tea plants (e.g., green tea leaf extract) may be included as a component of a composition of the disclosure. Such a composition has evidenced strong antioxidant benefits and wound healing properties. Other members of the *Camellia* genus may be processed to produce active agents that may be used in the composition of the disclosure.

Accordingly, in a particular embodiment, a composition of the disclosure includes as an active agent a component that is derived from at least one plant variety selected from the *Lycium, Punica, Vitis, Aspalathus*, and/or *Camellia* genus of plants. For instance, in certain variations, a composition of the disclosure includes as an active agent a component that is derived from at least one plant variety selected from the *Lycium barbarum, Punica granatum, Vitis vinifera, Aspalathus linearis*, and/or *Camellia Sinensis* species of plants. In certain variations, a composition of the disclosure includes as an active agent a component that is derived from at least one of goji berry, pomegranate, grape seed, red tea, white tea, green tea, and/or black tea. In certain variations, a composition of the disclosure includes as an active agent a component that is derived from at least two of goji berry, pomegranate, grape seed, red tea, white tea, green tea, and/or black tea. In certain variations, a composition of the disclosure includes as an active agent a component that is derived from at least three of goji berry, pomegranate, grape seed, red tea, white tea, green tea, and/or black tea. In certain variations, a composition of the disclosure includes as an active agent a component that is derived from at least four of goji berry, pomegranate, grape seed, red tea, white tea, green tea, and/or black tea. In certain variations, a composition of the disclosure includes as an active agent a component that is derived from at least five of goji berry, pomegranate, grape seed, red tea, white tea, green tea, and/or black tea. In certain variations, a composition of the disclosure includes as an active agent a component that is derived from at least six or seven of goji berry, pomegranate, grape seed, red tea, white tea, green tea, and/or black tea.

In one embodiment, the active agent is a liquid, finely ground powder, or an extract derived from a component of one or more of the above listed plant varieties. Accordingly, a composition of the disclosure may include as active agents components from any or all of the plant varieties set forth above in any quantity, or combination, suitable to give the desired oxidant, alleviating, and/or skin rejuvenating effect when applied topically.

The cosmetic compositions of the present disclosure are formulated for topical use. Accordingly, in a particular embodiment, a component from the one or more plant varieties detailed herein may serve as an active agent and may be incorporated into a topical composition by itself or in combination with one or more of the other plant derived active agents. In general, the subject cosmetic compositions contain at least about 0.001%, at least about 0.01%, at least about 0.1%, or at least about 1.0% and usually not more than about 10% (weight/weight), but sometimes as much as 20% or more of an active ingredient from one or more of the *Lycium, Punica, Vitis, Aspalathus*, and/or *Camellia* genus of plants. For instance, in certain variations, a composition of the disclosure may contain from about 0.001% to about 20% of an extract derived from one or more of *Lycium barbarum, Punica granatum, Vitis vinifera, Aspalathus linearis*, and/or *Camellia Sinensis* species of plants as an active ingredient. In certain variations, a composition of the disclosure may contain from about 0.001% to about 20% of an extract derived from all of *Lycium barbarum, Punica granatum, Vitis vinifera, Aspalathus linearis*, and *Camellia Sinensis* as an active ingredient. In certain variations, a composition of the disclosure may contain from about 0.001% to about 10% of an extract derived from one or more of goji berry, pomegranate, grape seed (e.g., grape seed oil), red tea, white tea, green tea, and/or black tea as an active ingredient.

Without being held to theory, the anti-aging effect of the composition of the disclosure stems in part from the synergistic antioxidant activities of its individual components, which may counteract the oxidative effects of free radicals, such as reactive oxygen species, which can lead to inflamed, irritated and dry skin and/or promote the generation of other skin-damaging free-radicals. As such, the cosmetic compositions of the present disclosure are uniquely suited to treat the conditions and disorders associated with the skin, including but not limited to: dermatitis, eczema, dry skin, sunburn, inflammation, pruritic lesions, and other inflammatory and non-inflammatory lesions of the skin. In some embodiments, the cosmetic compositions of the present disclosure are carefully formulated to provide one or more of the active agents in *Lycium barbarum, Punica granatum, Vitis vinifera, Aspalathus linearis*, and *Camellia Sinensis* in an active form, thereby maximizing its effectiveness of the overall composition.

In many embodiments, additional ingredients are included as part of the subject cosmetic compositions to enhance the synergistic effect of the active agents of the herbal compositions. Accordingly, one or more of the following ingredients may be included in a cosmetic formulation of the present invention.

Other Beneficial Agents

In certain variations, a composition of the disclosure may additionally include one or more other beneficial agents. For instance, in some embodiments, a cosmetic composition may include from about 0.001% to about 10% of an extract derived from one or more of the following plant varieties. *Vaccinium macrocarpon* (Cranberry), which may function within a cosmetic composition of the disclosure as an antioxidant, antibacterial, and/or antiseptic agent. *Citrus grandis* (Grapefruit), which may function within a cosmetic composition of the disclosure as an antioxidant, antibacterial agent, as well as for cleansing and/or exfoliating the skin. *Helianthus annuus* (Sunflower seed oil), which may function within a cosmetic composition of the disclosure as an emollient for rejuvenating the skin. Radish root ferment filtrate and Algae extract, which may function within a cosmetic composition of the disclosure as antimicrobial agents.

Other beneficial agents that may be included in a composition of the disclosure include fruit extract, *Panax ginseng* root (e.g., for skin conditioning), *Rosa canina* (e.g., as a source of Vitamin C), *Chondrus crispus* (e.g., for moisturizing the skin), *Simmondsia chinensis* seed extract (e.g., for skin conditioning), *Chamomilla recutita* flower extract (e.g., for one or more of relaxing, cleansing, moisturizing, and/or soothing the skin), *Aspalathus linearis* extract, which may act as an antioxidant, and *Helianthus annuus*. (e.g., for moisturizing the skin).

Skin Soothing/Conditioning Agents

The cosmetic compositions of the present invention may also contain agents that sooth, condition and/or rejuvenate the skin. One such agent is panthenol, a pro-vitamin moisturizing agent. Panthenol may be incorporated into cosmetic formulations and may function within a cosmetic composition of the disclosure by readily penetrating the skin to help deliver the active agents to a site of action and to sooth and moisturize the skin. Panthenol derivatives (e.g., ethyl panthenol) may also be used in the compositions of the disclosure as well as other agents such as provitamins B5 and E, as well as their derivatives, aloe vera (e.g., for soothing the skin), allantoin (e.g., for both soothing and softening of the skin), bisabolol (e.g., for soothing the skin), dipotassium glycyrrhizinate, pantothenic acid and its derivatives, as well as Sorbitol (e.g., for moisturizing the skin). A variety of emollients may also be included, such as Neopentyl Glycol Dicaprylate/Dicaprateester, Dimethicone, Tridecyl Trimellitate, and other such suitable emollients known in the art. Other skin conditioning/soothing agents can be included in the subject compositions, some of which are discussed below. The skin soothing and/or conditioning agents may be present at a concentration of at least about 0.01% or more, including about 0.25% or more, such about 0.5% or more, for instance about 1.0% to about 10% or more, such as about 20% or more.

Optional Skin Benefit Materials and Cosmetic Adjuncts

The compositions of the disclosure may optionally include other beneficial materials. These may include steroidiol hormones; progesterone; pregnanalone; coenzyme Q10; methylsolanomethane (MSM); sodium phytate (which may function as a chelating and/or stabilizing agent); copper peptide (copper extract); plankton extract (phytosome); transforming growth factor beta 1 (TGF-β1); glycolic acid; kojic acid; ascorbyl palmitate; all-trans-retinol; azaleic acid; salicylic acid; analgesics; non-steroidal anti-inflammatory drugs (NSAIDs); broparoestrol; and the like. If present, steroids may be present at a concentration of less than about 2% of the total by weight of the composition, while the other optional skin benefit materials may be present at higher levels, for example as much as 10 to 15%.

The compositions may further include sunscreens to lower skin's exposure to harmful UV rays. Sunscreens may include those materials commonly employed to block ultraviolet light. Exemplary compounds are the derivatives of PABA, cinnamate and derivatives of salicylate (other than ferulyl salicylate). For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. Dermascreen may also be used. Additionally, a composition may further include aloe vera or an extracted component or powder thereof, such as anthraquinone glycosides, resins, polysaccharides, sterols, gelonins, and chromones. The exact amount of sunscreen or aloe employed in the compositions can vary depending upon the degree of protection desired from the sun's UV radiation.

The cosmetic compositions of the present invention may also contain benzoyl peroxide, which may act synergistically with the various herbal active agents in various cosmetic compositions of the disclosure to treat aging-related conditions and/or disorders. Benzoyl peroxide is a commonly used topical treatment for mild acne. Benzoyl peroxide has antiseptic properties, i.e., it reduces the number of skin surface bacteria and yeast; is an oxidizing agent, making it keratolytic and comedolytic; and has anti-inflammatory activity. The cosmetic compositions may contain benzoyl peroxide at concentrations contain at least about 1%, at least about 2.5%, at least about 5%, and usually not more than about 10% (weight/weight). Benzoyl peroxide is commercially available as a cream, gel, lotion, or wash under the following brand names: Benoxyl™, Benzac™, Brevoxyl™, Oxy™ and PanOxyl™.

Cosmetically Acceptable Vehicle

The compositions of the disclosure may include a cosmetically acceptable vehicle to act as a dilutent, dispersant or carrier for the active ingredients, so as to facilitate its distribution and uptake when the composition is applied to the skin. Vehicles other than or in addition to water can include liquid or solid emollients, solvents, humectants, thickeners, powders, and perfumes, some of which have been described above. For instance, a suitable carrier may include, for example, glycerin, butylene glycol, propylene glycol, water, various oils (jojoba, sweet almond, soybean, sunflower, apricot, etc.), and the like.

The cosmetically acceptable vehicle may range form from about 1% or less to about 99.9% or more, such as from about 10% to about 90%, including about 25% to about 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

When the compositions of the invention are formulated as an emulsion, the proportion of the fatty phase may range from about 5% or less to about 80% or more by weight, such as from about 10% to about 50% by weight, relative to the total weight of the composition. Oils, emulsifiers and co-emulsifiers incorporated in the composition in emulsion form are selected from among those used conventionally in the cosmetic or dermatological field. The emulsifer and coemulsifier may be present in the composition at a proportion ranging from about 0.3% or less to about 30% or more by weight, such as from about 0.5% to about 20% by weight, relative to the total weight of the composition.

When the compositions of the invention are formulated as an oily solution or gel, the fatty phase may constitute more than about 50% or less, more than about 60%, more than about 70%, more than about 80%, more than about 90% of the total weight of the composition.

The compositions of the invention may be in the form of body cleansing compositions. As such, these compositions may contain one or more wash-active surfactant in an aqueous base. The surfactants can be present, alone or in a mixture, and are contained in an amount of from about 1% or less to about 50% or more by weight or from about 1% or less to about 30% or more by weight. Nonionic surfactants, amphoteric surfactants, zwitterionic surfactants and anionic surfactants are generally suitable.

Suitable anionic surfactants include, e.g. alkaline or alkaline earth salts, alpha-olefin sulfonates, sulfosuccinates, disodium laureth-3 sulfosuccinate, disodium PEG-5 lauryl citrate sulfosuccinate, disodium ricinolamido MEA-sulfosuccinate or disodium laurylamido MEA-sulfosuccinate and alkyl ether carboxylates.

Suitable nonionic surfactants include e.g., alkoxylated fatty alcohols, alkoxylated fatty acid esters, alkoxylated partial glycerides, saturated or unsaturated fatty acids, alkoxylated polyol esters, and alkylpolyglucosides, such as coconut glucosides, lauryl glycosides or decylglucosides. For example, ethoxylated lauryl alcohol, tetradecyl alcohol, cetyl alcohol, oleyl alcohol or stearyl alcohol, which are used alone or in mixtures with each other, as well as fatty alcohols of ethoxylated lanolin, are suitable as fatty alcohol ethoxylates. Furthermore the ethoxylated fatty acid sugar esters known as nonionic surfactants, especially ethoxylated sorbitan fatty acid ester, are suitable for use in the cosmetic preparations according to the invention. The suitable ethoxylated fatty acid sugar esters include those marketed under the trade names Tween™ and Arlacel™ by ICI surfactants and the alkylpolyglycosides, which are marketed under the trade names Plantaren™ or Plantacare™ by Henkel or under the trade name Oramix™ by Seppic. Suitable amphoteric surfactants include for example betaines, such as cocoamidopropylbetaine or lauryl betaine, sulfobetaines, such as cocoamidopropyl hydroxysultaine, glycinates, such as cocoamphoglycinate (INCI-name: sodium cocoamphoacetate) and diglycinates and propionates, such as cocoampho-propionate.

The compositions of the disclosure may also include additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, perfumes, fillers, bactericides, odor absorbers and dyestuffs or colorants. The amounts of these various additives and adjuvants are those conventionally used in the field, and, for example, range from about 0.01% or less to about 10% or more of the total weight of the composition. Depending on their nature, these additives and adjuvants may be introduced into the fatty phase or into the aqueous phase.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate (e.g., to help the oil and water phases combine), polysorbate 60, PEG-6/PEG-32/glycol stearate mixture, etc. Solvents which may be used include the lower alcohols, in particular ethanol and isopropanol, and propylene glycol. Suitable fatty alcohols and acids include those compounds having from 10 to 20 carbon atoms. For instance, compounds such as cetyl, myristyl, palmitic and stearyl alcohols and acids. For example, cetearyl alcohol and ceteareth 20, as well as cetyl alcohol and stearyl alcohol-fatty alcohols may also be included.

Hydrophilic gelling agents include carboxyvinyl polymers (carbomer), acrylic copolymers, such as acrylate/alkylacrylate copolymers, polyacrylamides, polysaccharides, such as hydroxypropylcellulose, natural gums and clays (such as Xanthan gum), and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present disclosure are thickeners. A thickener may be present in amounts anywhere from about 0.1% or less to about 20% or more by weight, such as from about 0.5% to about 10% by weight of the composition. Exemplary thickeners may be cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the disclosure. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from about 0.001% or less up to about 20% or more by weight of the composition.

Product Use, Form, and Packaging

In use, a quantity of the composition, for example from about 1 ml or less to about 100 ml or more, is applied to a site of interest (e.g., skin, scalp, etc.) from a suitable container or applicator and, if necessary, it is then spread over and/or rubbed into the site using the hand or fingers or a suitable device, such as a brush, comb, or other suitable applicator. The composition may be specifically formulated for use as a treatment for a specific area, e.g. the hands, the face, the scalp, the feet, etc.

The cosmetic composition of the disclosure may be formulated in any form suitable for application to the site of interest, including a lotion, cream, gel, shampoo, etc. The composition can be packaged in a suitable container to suit its viscosity and intended use by the consumer. For example, a lotion or cream can be packaged in a bottle, or a propellant-driven aerosol device or a container fitted with a pump suitable for finger operation. When the composition is a cream, it can simply be stored in a non-deformable bottle or squeeze container, such as a tube or a lidded jar. The disclosure accordingly also provides a closed container containing a cosmetically acceptable composition as herein defined.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

EXAMPLE 1

Example 1 illustrates topical compositions according to the present invention. The compositions can be processed in accordance with conventional manners well known in the art. They are suitable for cosmetic use. In particular the compositions are suitable for application to a site of interest that has an aging-related condition or disorder. Application of the cosmetic compositions will combat these conditions thereby restoring a more youthful appearance. In addition, certain of these cosmetic compositions can be used to prevent the onset of the aging-related condition or disorder.

| OIL-IN-WATER EMULSION | |
|---|---|
| Ingredient | % w/w |
| DI Water | QS |
| Carbomer | 0.10-2.00 |
| Sodium Phytate | 0-0.20 |
| Glycerin | 0-10.00 |
| Polysorbate 20 | 0-10.00 |
| Butylene Glycol | 0-10.00 |
| Triethanolamine 99% | 0-1.50 |
| Isopropyl Myristate | 0-10.00 |
| Octyl Palmitate | 0-10.00 |
| Cetyl Alcohol | 0-5.00 |
| Dimethicone 100 cst | 0-10.00 |
| Beeswax | 0-5.00 |
| Propylparaben | 0-0.50 |
| Germall II | 0-0.50 |
| Fragrance | 0-5.00 |
| Total | 100.00 |

| OIL-IN-WATER EMULSION | |
|---|---|
| Ingredient | % w/w |
| DI Water | QS |
| Xanthan Gum | 0-2.00 |
| Sodium Phytate | 0-0.20 |
| Glycerin | 0-10.00 |
| Burylene Glycol | 0-10.00 |
| Isopropyl Myristate | 0-10.00 |
| Octyl Palmitate | 0-10.00 |
| Cetyl Alcohol | 0-3.00 |
| Dimethicone 100 cst | 0-10.00 |
| Steareth-2 | 0-5.00 |
| Steareth-21 | 0-5.00 |
| Propylparaben | 0-0.50 |
| Germall II | 0-0.50 |
| Fragrance | 0-5.00 |
| Total | 100.00 |

| WATER-IN-OIL EMULSION | |
|---|---|
| ingredient | % w/w |
| DI Water | QS |
| Sodium Phytate | 0-0.20 |
| Glycerin | 0-10.00 |
| Propylene Glycol | 0-10.00 |
| Sodium Chloride | 0-2.00 |
| Cyclomethicone | 0-10.00 |
| Isopropyl Myristate | 0-10.00 |
| Octyl Palmitate | 0-10.00 |
| Dimethicone Copolyol | 0-10.00 |
| Dimethicone 100 cst | 0-10.00 |
| Beeswax | 0-5.00 |
| Propylparaben | 0-0.50 |
| Germall II | 0-0.50 |
| Fragrance | 0-5.00 |
| Total | 100.00 |

| HYDRO-GEL | |
|---|---|
| Ingredient | % w/w |
| DI Water | QS |
| Butylene Glycol | 5.00 |
| PPG-5-Ceteth 20 | 5.00 |

| HYDRO-GEL | |
|---|---|
| Ingredient | % w/w |
| Glycerin | 3.00 |
| Carbomer | 1.20 |
| Triethanolamine 99% | 1.20 |
| Methylparaben | 0.30 |
| Polysorbate 20 | 0.25 |
| Sodium Phytate | 0.10 |
| Germall II | 0.10 |
| Total | 100.00 |

| ANHYDROUS SERUM | |
|---|---|
| ingredient | % w/w |
| Cyclomethicone | QS |
| Isopropyl Myristate | 0-10.00 |
| Octyl Palmitate | 0-10.00 |
| Polyglycerol-6 Dioleate | 0-10.00 |
| Butylene Glycol | 0-10.00 |
| Dimethicone, 100 cst | 0-10.00 |
| Beeswax | 0-5.00 |
| Propylparaben | 0-0.50 |
| Fragrance | 0-5.00 |
| Total | 100.00 |

| HYDRO-ALCOHOLIC GEL | |
|---|---|
| ingredient | % w/w |
| DI Water | QS |
| Alcohol SDA40B | 0-50.00 |
| Butylene Glycol | 0-10.00 |
| PPG-5-Ceteth 20 | 0-5.00 |
| Glycerin | 0-10.00 |
| Carbomer | 0-2.00 |
| Triethanolamine 99% | 0-1.50 |
| 4-chromanone | 0-2.00 |
| Polysorbate 20 | 0-5.00 |
| Sodium Phytate | 0-0.20 |
| Germall II | 0-0.50 |
| Total | 100.00 |

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cosmetic composition for topical application to the skin comprising a blend of extracts in the following amounts based upon weight % of the total dry weight of the composition:

0.01% to 20% by weight *Lycium barbarum;*
0.01% to 20% by weight *Punica granatum;*
0.01% to 20% by weight *Vitis vinifera;*
0.01% to 20% by weight *Aspalathus linearis;*

0.01% to 20% by weight of *Camellia sinensis*; and a cosmetically acceptable vehicle, wherein the blend of extracts provides a protective effect against free radicals formed by exposure to ultraviolet light in human skin.

2. The composition of claim 1, wherein the cosmetic composition further comprises an active agent derived from one or more members selected from the group consisting of: *Vaccinium macrocarpon*, Citrus grandis, *Helianthus annuus*, Radish root ferment filtrate, Fruit extract, *Panax ginseng* root, *Rosa canina, Chondrus crispus*, Algae extract, Simmondsia chinensis seed extract, *Chamomilla Recutita* flower extract, Aspalathus linearis extract, and *Helianthus annuus*.

3. The cosmetic composition according to claim 1, wherein the *Vitis vinifera* extract is an extract derived from a seed of the *Vitis vinifera* plant.

4. The cosmetic composition according to claim 1, wherein the *Vitis vinifera* extract comprises an oil derived from the seed of the *Vitis vinifera* plant.

5. The cosmetic composition according to claim 1, wherein the *Camellia Sinensis* extract comprises one or more of white tea, green tea, black tea, and oolong.

6. The cosmetic composition according to claim 5, wherein the *Camellia Sinensis* comprises at least green tea and black tea.

7. The composition according to claim 1, wherein said cosmetically acceptable vehicle is an oil in water, or water in oil emulsion.

8. The composition according to claim 1, wherein said cosmetically acceptable carrier is a member selected from the group consisting of glycerin, butylene glycol, propylene glycol, water, jojoba oil, sweet almond oil, soybean oil, sunflower oil, and apricot oil.

9. The composition according to claim 1, wherein said composition further comprises a sunblock.

10. The composition of claim 1, where the composition does not include one or more of a paraben, a preservative, a petro chemical, a synthetic dye, or a sulfate.

11. A method for providing protective effects against free radicals formed by exposure to ultraviolet light in human skin comprising topically administering to the skin of a subject in need thereof the cosmetic composition of claim 1.

* * * * *